United States Patent [19]

Akkas et al.

[11] Patent Number: 4,909,249
[45] Date of Patent: Mar. 20, 1990

[54] SURGICAL CUTTING INSTRUMENT

[75] Inventors: Tamer Akkas; Ted Carlson, both of Mission Viejo, Calif.

[73] Assignee: The Cooper Companies, Inc., Menlo Park, Calif.

[21] Appl. No.: 116,796

[22] Filed: Nov. 5, 1987

[51] Int. Cl.4 ............................................. A61F 17/32
[52] U.S. Cl. ................................. 606/107; 128/753; 604/22; 606/171
[58] Field of Search .................. 128/305, 751–755; 604/22

[56] References Cited

U.S. PATENT DOCUMENTS

| | | | |
|---|---|---|---|
| 3,776,238 | 2/1973 | Peyman et al. | 128/305 |
| 3,815,604 | 4/1974 | O'Malley et al. | 128/305 |
| 3,884,238 | 9/1975 | O'Malley et al. | 128/305 |
| 3,994,297 | 12/1976 | Kopf | 128/276 |
| 4,011,869 | 7/1977 | Seiler, Jr. | 128/276 |
| 4,099,529 | 1/1978 | Peyman | 128/305 |
| 4,111,207 | 3/1978 | Seiler, Jr. | 128/305 |
| 4,200,106 | 3/1980 | Douvas et al. | 128/305 |
| 4,246,902 | 8/1981 | Martinez | 128/305 |
| 4,314,560 | 2/1982 | Helfgott et al. | 128/305 |
| 4,316,465 | 1/1982 | Dotson, Jr. | 128/276 |
| 4,428,748 | 7/1984 | Peyman et al. | 604/22 |
| 4,449,550 | 9/1984 | Ranalli | 137/624.13 |
| 4,530,356 | 3/1985 | Helfgott et al. | 128/305 |
| 4,570,632 | 2/1986 | Woods | 128/305 |
| 4,577,629 | 7/1986 | Martinez | 128/305 |
| 4,601,290 | 7/1986 | Effron et al. | 128/305 |
| 4,674,502 | 4/1987 | Imonti | 128/305 |
| 4,681,123 | 7/1987 | Valtcher | 128/753 |
| 4,696,298 | 11/1987 | Higgins et al. | 128/305 |

OTHER PUBLICATIONS

"MicroVit Vitrectomy System", Copyright 1983.
Int'l Publication No: WO 81/01363, "Cozxial Tube Surgical Suction Cutter Tip" 1981.

Primary Examiner—Max Hindenburg
Attorney, Agent, or Firm—Vorys, Sater, Seymour and Pease

[57] ABSTRACT

A surgical cutting instrument such as for use in intraocular surgery having a handpiece with an elongate probe extending foward from it. The probe has an elongate stationary outer cutter with a port at its tip and an elongate inner cutter with a cutting surface coaxially disposed therein. The interior of the inner cutter communicates with a vacuum source. A spring and diaphragm assembly in the handpiece and powered by a low pressure pump causes the inner cutter to rapidly reciprocate axially in the outer cutter, and body material, such as vitreous material, drawn in through the port by the vacuum source is thereby chopped by the cutting surface and aspirated out of the patient's body through the handpiece. A large adjustment nut on the handpiece allows the size of the port to be easily adjusted. Irrigation fluid can be provided at the surgical site through an infusion cap which is adjustable both longitudinally and rotatably on the handpiece.

34 Claims, 6 Drawing Sheets

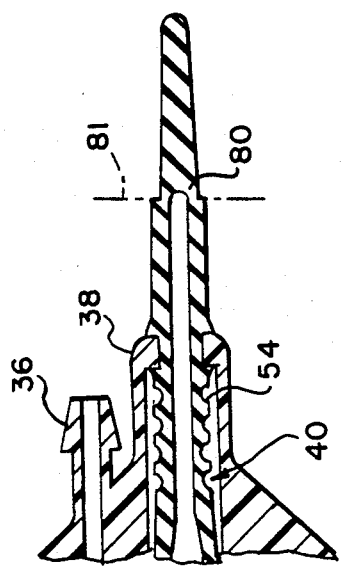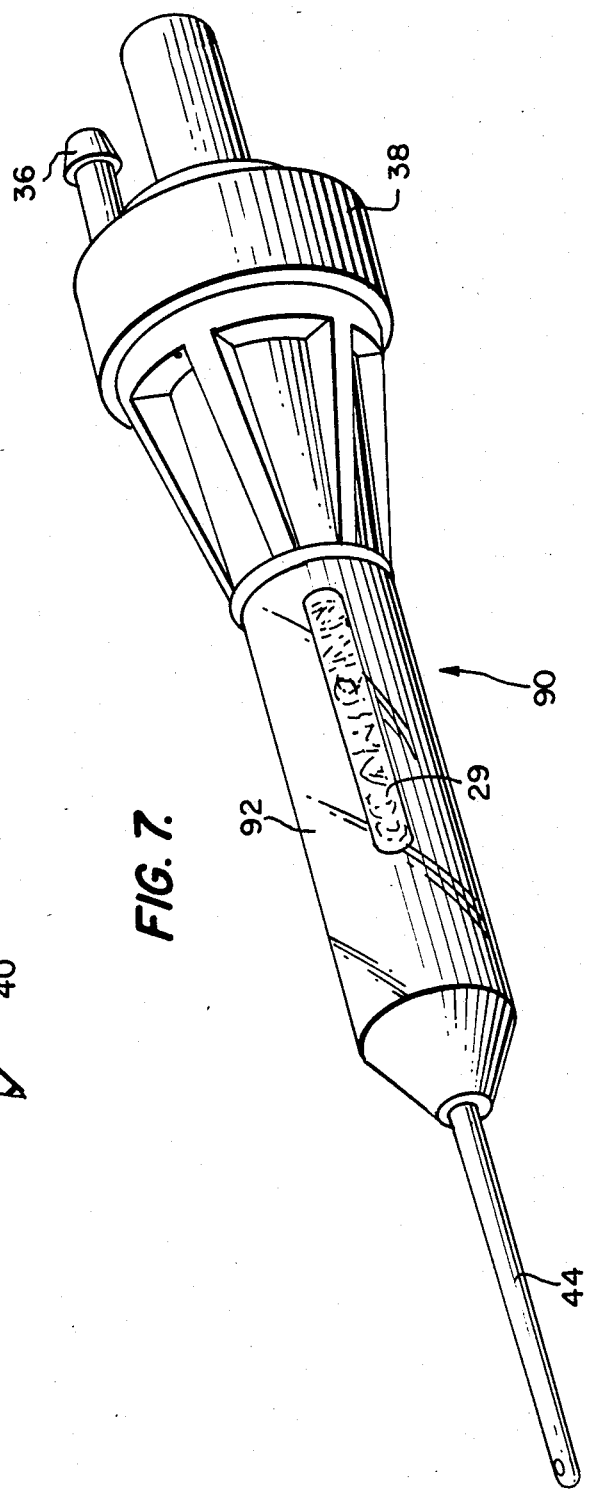

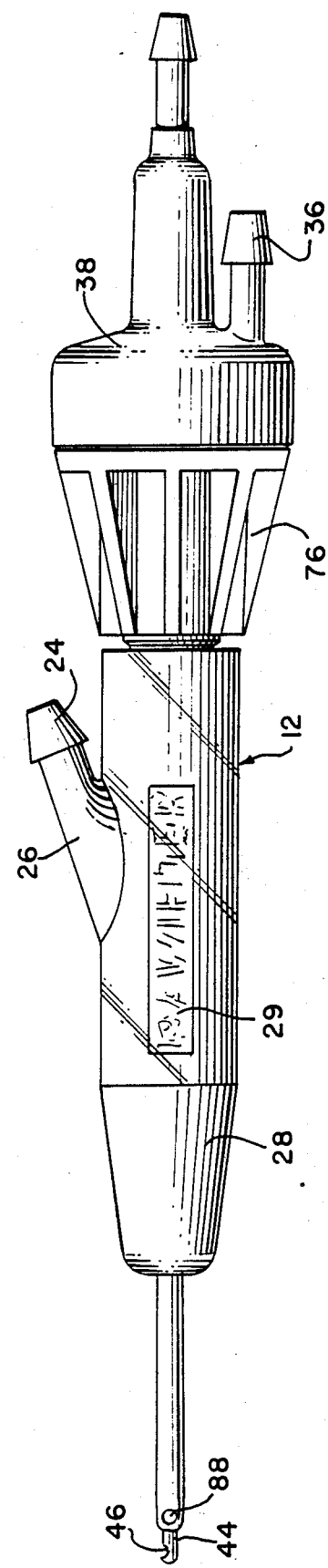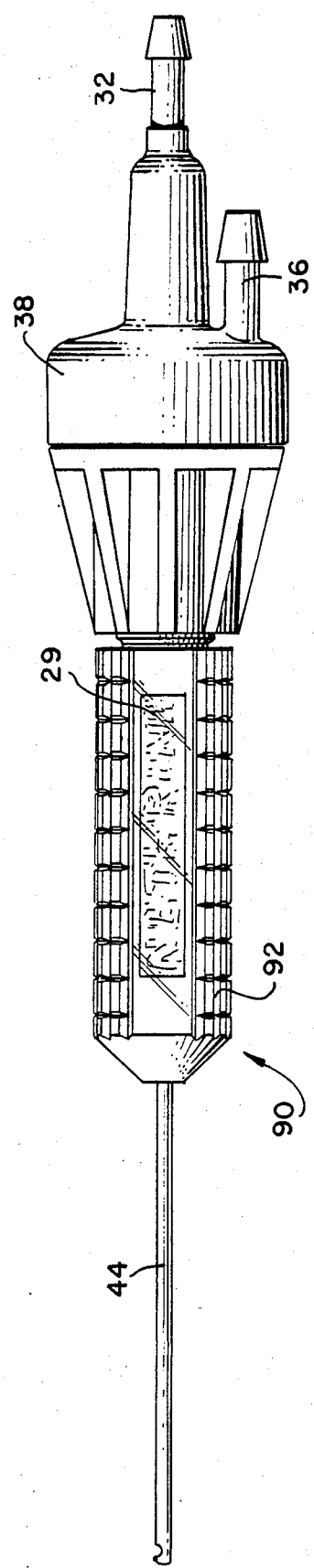

SURGICAL CUTTING INSTRUMENT

BACKGROUND OF THE INVENTION

The present invention relates to surgical cutting instruments and more particularly to surgical cutting instruments used in ophthalmic surgery. It further relates to surgical cutting instruments for use in cutting and evacuating material from parts and organs of animal and human bodies. It also pertains to vitrectomy handpieces for providing irrigating and aspirating and cutting functions for cutting and removing vitreous, blood clots and other material from the eye during intraocular surgery, and to such handpieces which more particularly incorporate reciprocating cutters.

Many surgical instruments have been designed in the recent past to said ophthalmic surgeons in removing vitreous, blood clots, cataracts, lenses and other matter from the eye. These instruments typically have an elongated probe defining a cutter at the distal end thereof, which is inserted into the body, for example into the eye through an incision in the cornea or sclera. The probe thereof is typically formed by coaxial inner and outer tubes wherein a port is provided in the outer tube adjacent the end and the inner tube moves relative thereto, and the inner and outer tubes cut the material as it is drawn in through the port. The excised tissue is aspirated by suction from the interior of the body part, such as the eye, possibly together with fluid, through the central lumen of the hollow inner tube, and is collected in a collection vessel.

It has been found that when the inner tube motion is rotational relative to the outer tube that the vitreous and other materials are pulled or sheared while being cut. Thus, the current practice is to provide for the inner tube to reciprocate longitudinally relative to the outer tube and thereby provide a chopping or guillotine type of action to cleanly cut the vitreous body. Many methods are known for effecting this reciprocating movement of the inner cylinder including utilizing an electric motor or a pneumatic actuator positioned in the handpiece, and these include the devices disclosed in U.S. Pat. No. 4,246,902, to Martinez, and U.S. Pat. No. 4,674,502, the entire contents of both of which are hereby incorporated by reference. It is also known to use a bellows positioned in the handpiece with the inner cutting tube being secured to the bellows, and a means for alternately supplying compressed air and vacuum to the bellows. This arrangement is shown for example in U.S. Pat. No. 3,884,238, whose entire contents are also hereby incorporated by reference. It is further known to include on the surgical cutting tool an infusion sleeve or similar means for providing irrigation either during or separately from the cutting procedure. This irrigation means can bathe the surgical site in a physiological fluid and for ophthalmic surgery can maintain the intraocular pressure to prevent the collapse of the eyeball.

These known cutting instruments though suffer from many disadvantages, including the difficulty in assembling them, excessive vibrations created by the handpiece, inability to attain cutting speeds greater than 600 cuts per minute, lack of suitable means for adjusting the size of the cutting and aspirating port, and the presence of outside moving parts on the handpiece. Thus, a need has arisen for an improved design for such surgical cutting instruments.

Accordingly, it is a principal object of the present invention to provide an improved design for a surgical cutting instrument.

Another object of the present invention is to provide an improved surgical cutting instrument construction which can be easily assembled and is designed to be economically disposable after a single use.

A further object of the present invention is to provide an improved construction of a surgical cutting instrument having an infusion component which can be easily adjusted.

A still further object of the present invention is to provide an improved surgical cutting instrument design which reduces the vibrations created by the handpiece thereof.

Another object is to provide an improved vitrectomy handpiece having no moving parts outside of the body of the handpiece.

A further object is to provide an improved surgical cutting instrument having greater cutting speeds for increased efficiency and safety.

Other objects and advantages of the present invention will become apparent to those persons of ordinary skill in the art from the foregoing description taken in conjunction with the accompanying drawings.

BRIEF DESCRIPTION OF THE DRAWINGS

FIG. 4 is a fragmentary, cross-sectional view of the proximal end of the handpiece illustrating the proximal end of the diaphragm after being threaded through the end cap.

FIG. 5 is an elevational view of the handpiece of the surgical cutting instrument of FIG. 1.

FIG. 6 is an elevational view of a posterior vitrectomy handpiece variant of the surgical cutting instrument of FIG. 1.

FIG. 7 is a perspective view of the posterior vitrectomy handpiece of FIG. 6.

DETAILED DESCRIPTION OF THE PREFERRED EMBODIMENTS

Figure 1:
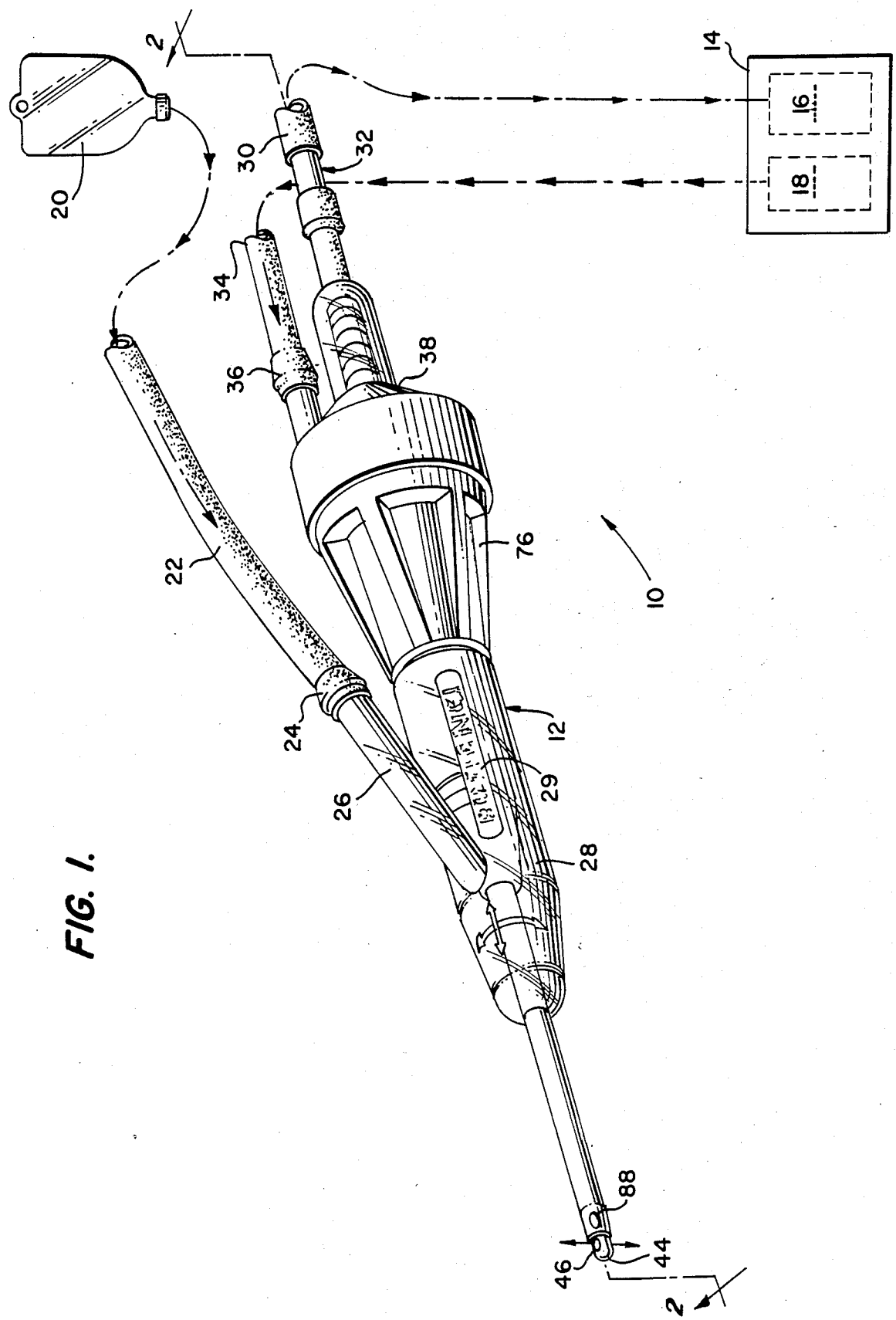
FIG. 1 is a perspective view of a surgical cutting instrument of the present invention with the handpiece thereof shown enlarged for the sake of clarity.

Referring to the drawings a preferred surgical cutting instrument of the present invention is illustrated generally at 10. Instrument 10 is shown in FIG. 1 to comprise a vitrectomy handpiece illustrated generally at 12 connected to a low pressure twenty to thirty psi pump illustrated schematically at 14 providing a vacuum source 16 and a pressure source 18, and an irrigation source 20, such as a BSS bottle located at a predetermined height above the surgical site, providing a source of irrigation fluid. The bottle 20 is connected by a silicone or PVC tubing 22 to the infusion fitting 24 on the infusion sleeve 26 portion of the infusion cap 28. A logo pad 29 to display the manufacturer's or distributor's logo is provided on and along the infusion cap 28. A silicone tubing vacuum line 30 is provided from the vacuum source 16 to the vacuum fitting 32 of the handpiece 12, and a silicone tubing pressure line 34 connects to a pressure line fitting 36. The vacuum fitting 32 and the pressure fitting 36 are both attached generally at separate locations to the distal end of the end cap 38 of the handpiece 12.

The end cap 38 which is formed is formed of a medical grade plastic houses a diaphragm assembly shown generally at 40 (FIG. 2), and the diaphragm assembly 40 is secured to the inner cutting tube 42 which is adapted to reciprocate within the outer cutting tube 44. The outer cutting tube 44 has a side port 46 adjacent its forward tip and has a cutting surface, and the inner cutting tube 42 has a cutting surface 47 at its distal tip which slides reciprocally relative to the port 46. Inner cutting tube 42 is hollow so that when suction is applied to it through the fitting 32, vitreous and other matter is drawn into the port 46 and the reciprocating inner cutting tube 42 chops the matter drawn into the port 46 in a quillotine fashion, and then aspirated out the inner cutting tube 42 through the vacuum line 30, as illustrated for example in U.S. Pat. No. 3,776,238, which is hereby incorporated herein.

Simply explained, the diaphragm assembly 40 is caused to reciprocate back and forth by the action of pressurized air through the pressure line 34 against the diaphragm assembly 40 in a forward direction, and the bias to the diaphragm assembly 40 in the opposite rearward direction is caused by the compressed bias spring 48 disposed in the chamber 50 of the assembly tip and body member 52 and also by the vacuum effect thereon from the vacuum source 16. The assembly tip and body member 52 can be also made from a medical grade plastic.

Figure 2:
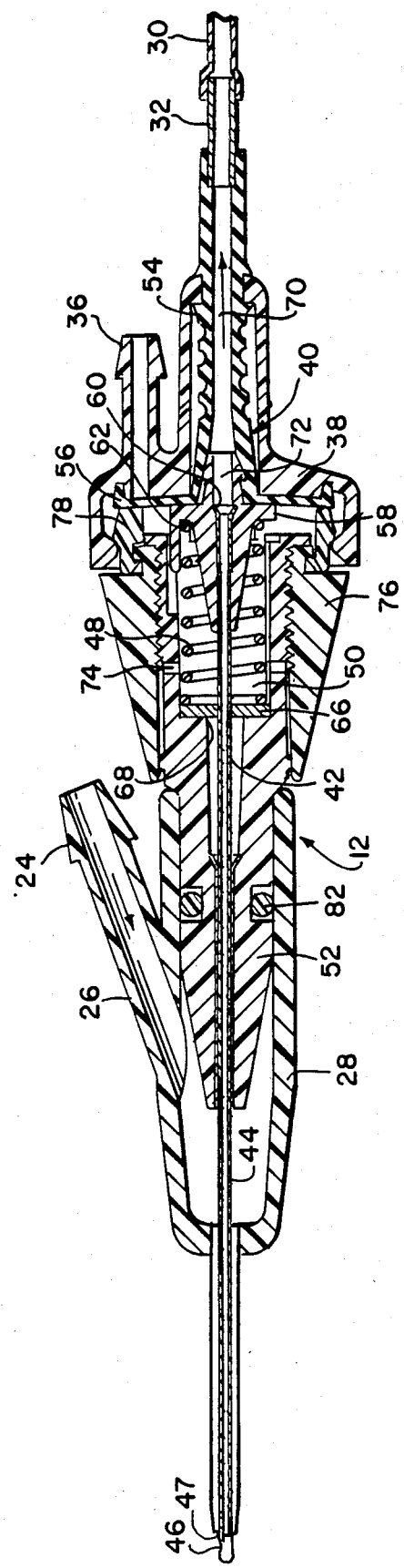
FIG. 2 is a cross-sectional view of the handpiece of the surgical cutting instrument of FIG. 1 taken along line 2—2 and illustrated in isolation.
Figure 3:
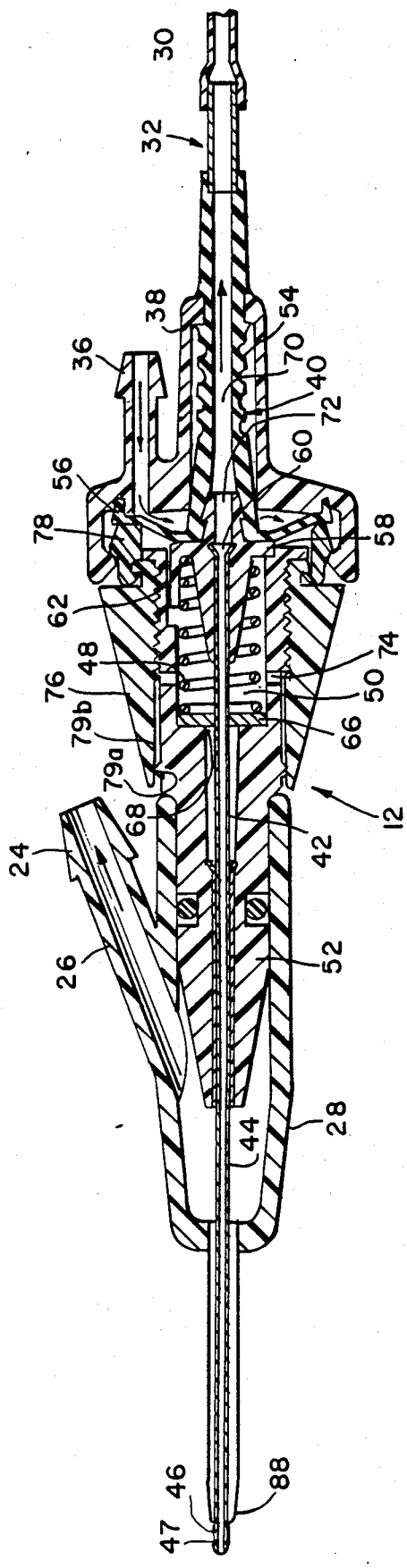
FIG. 3 is a view similar to FIG. 2 illustrating the components of the handpiece in their extended position.

The diaphragm assembly 40 in its retracted position is best illustrated in FIG. 2 and in its extended position in FIG. 3. It is seen from those figures that the diaphragm assembly 40 which is formed of silicone has a proximal expandable and contractable bellows portion 54, an integral diaphragm flange 56, and a separate diaphragm hub 58 disposed forward of the diaphragm flange 56 and in which the inner cutting tube 42 is secured by tube proximal outwardly-flaring flange 60. The bias spring 48 has its rearward end seated in the seat 62 formed by the diaphragm hub 58 and its forward end positioned against gasket 66. Gasket 66 in turn is sandwiched between the bottom of the major hole 68 in the body member 52 and the bias spring 48, and is provided to prevent air bubbles from forming in the vacuum line 30 by blocking air from passing between the inner and outer cutting tubes 42, 44. The diaphragm assembly 40 has a diaphragm passageway 70 passing longitudinally therethrough as does the diaphragm hub 58 with its hub passageway 72, both of which define a passageway communicating the interior of the inner cutting tube 42 with the vacuum line 32 and through which a vacuum pressure is applied and out through which the cut vitreous materials are aspirated.

Thus, during the reciprocating cycle when the pressure in the pressure line 34 is not at its peak the spring 48 and the alternating sucking force in the pressure line 34 cause the diaphragm assembly 40, and thus the inner cutting tube 42 secured thereto and the spring, to be positioned in their rearward position, as best illustrated in FIG. 2. In this position the port 46 is open so that vitreous material can be sucked therethrough and into the tip of the inner cutting tube 42. Then when the pressure in the pressure line 34 is increased the pressurized air causes the diaphragm bellows portion 54 to expand and the diaphragm hub 58 to be pushed forward against the bias of the spring 48. The inner cutting tube 42 secured to the hub 58 is thereby caused to move forward so that its cutting surface 47 passes in front of the port 46 and chops the drawn-in vitreous material. This forward position is best illustrated in FIG. 3. As the diaphragm moves forward, the air in the chamber 50 is expelled out of the body member 52 through relief holes 74, and sucked in through them when the diaphragm moves backward. The relief holes 74 are positioned so that they cannot be closed off as by the user's fingers or by other means.

Adjustments to the size of the port 46 can be made by holding the end cap 38 against rotation and turning clockwise or counterclockwise relative to the body member 52 the adjustment nut 76, which is threaded on the aft portion of the body member 52 and formed of a medical grade plastic. An annular adapter 78 also formed of a medical grade plastic is snap fitted tightly to the end cap 38, and thus, as the adjustment nut 76 is turned, the adapter 78, the end cap 38 and the diaphragm hub 58 are all moved forward or backward depending on the direction in which the adjustment nut 76 is turned. As the diaphragm hub 58 is moved relative to the body member 52, the longitudinal normal position of the inner cutting tube 42 relative to the outer cutting tube 44 is also adjusted. Due to this design the forward and backward movements of the diaphragm assembly 40 can be repeated up to eight hundred times a minute, which is considerably greater than the six hundred times per minute rate possible with most commercially-available surgical cutting instruments. The rotary movement of the adapter 78, diaphragm hub 58, and end cap 38 is prevented by built-in orientation means.

The body member 52 has two round dimples 79a, spaced one hundred and eighty degrees apart. The adjustment nut 76 has twelve longitudinal lips 79b equally spaced on the internal surface between the threads and the distal end. The radial distance between two opposite lips is slightly smaller than the distance between the dimples. A click can be heard each time the adjustment nut 76 is turned thirty degrees in either the clockwise or the counterclockwise direction as the lips 79b of adjustment nut 76 are forced over the dimples 79a of body member 52.

The construction of the diaphragm assembly 40 is thus unique in that it provides a diaphragm, bellows, sealing and free passageway functions all in one unit. It expands and contracts in its bellows portion 54 thereby providing flexibility and eliminating the need for any (stainless steel) aspiration tubes sticking outside of the end cap 38 as found on many prior devices, and in fact no moving parts outside of the body member 52 of the vitrectomy handpiece 12 are needed. Also, the very end 80 of the diaphragm assembly 40 outside of the body member 52, as shown in FIG. 4, comprises an assembly aid to easily thread the diaphragm through the hole in the back of the end cap 38, and to be cut off as at location 81 after threading the diaphragm through that hole. The diaphragm flange 56 is sandwiched between the end cap 38 and the adapter 78 to provide a good seal therebetween. It has been found that the diaphragm assembly also creates less vibration during its operation than experienced with other similar handpieces.

The infusion cap 28 which is made of a medical grade plastic is adjustable in both longitudinal and circular directions relative to the body member 52, as indicated by the arrows in FIG. 1. An O-ring 82 provides a seal against the infusion fluid that comes in through the infusion fitting 24 and allows firm yet adjustable movements of the infusion cap 28 relative to the body member 52. The infusion or irrigation fluid then passes out the infusion sleeve 26 and out the coaxial opening 88 at the end of the sleeve adjacent the port 46.

Since no O-rings are needed in the reciprocating drive aspect of this instrument 10, reduced drag results, the instrument is easier to operate, a lower air pressure of only twenty to thirty psi of pump 14 is needed, and no silicone oil is needed. Also because the body parts are snap-fitted together, assembly of handpiece 12 is easy and reliable and no adhesives or the like are required.

Figure 8:
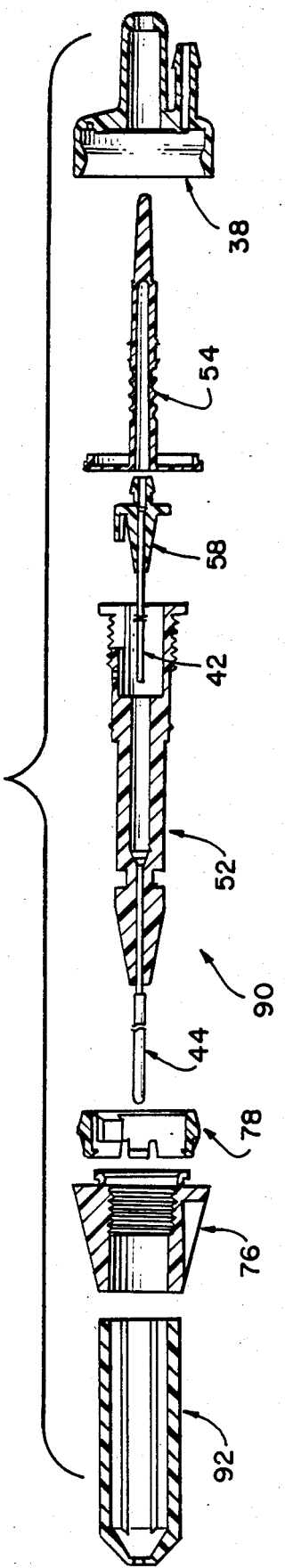
FIG. 8 is an exploded cross-sectional view of the posterior vitrectomy handpiece of FIG. 6 illustrating the major components thereof.

Although the primary use of the subject surgical cutting instrument 10 is for ophthalmic surgery, namely irrigation and aspiration, anterior vitrectomy and posterior vitrectomy, surgical uses on or in other parts of the body are possible, including liposuction, back surgery, kidney stone surgery, gall bladder surgery, orthopedic surgery and reconstructive plastic surgeries. An example of a posterior vitrectomy handpiece of the present invention is shown in FIGS. 6–8 generally at 90. Handpiece 90 corresponds generally to handpiece 12 except that it lacks an irrigation infusion capability and thus has a body sleeve construction as shown generally at 92 in place of the infusion cap 28.

From the foregoing detailed description it will be evident that there are a number of changes, adaptations and modifications of the present invention which come within the province of those persons having ordinary skill in the art to which the aforementioned invention pertains. However, it is intended that all such variations not departing from the spirit of the invention be considered as within the scope thereof as limited solely by the appended claims.

What is claimed is:

1. A surgical cutting instrument comprising:
   a diaphragm assembly connectable to a source of pressure,
   an inner cutter operatively connected to said diaphragm assembly, connectable to a source of vacuum, and defining a cutting surface,
   an outer cutter positioned outside of said inner cutter and defining a suction port,
   a biasing means for biasing said inner cutter against the bias caused by the force of the source of pressure on said inner cutter via said diaphragm assembly,
   said biasing means and the operation of the source of pressure causing said cutting surface to reciprocate relative to said port and to thereby cut the matter drawn into said port by the operation of the source of vacuum,
   an adjustment means connected to said inner cutter for adjusting the normal position of said cutting surface relative to said port, and
   a body member secured to said outer cutter, and said adjustment means comprising an adjustment nut threaded on said body member and operatively connected to said inner cutter such that as said adjustment nut is threaded on said body member the longitudinal position of said cutting surface relative to said port is adjusted.

2. The instrument of claim 1 wherein said diaphragm assembly comprises a diaphragm and a diaphragm hub connected to said diaphragm and positioned generally forward thereof.

3. The instrument of claim 2 wherein said inner cutter is secured in said diaphragm hub.

4. The instrument of claim 2 wherein said biasing means comprises a spring which biases against said hub.

5. The instrument of claim 4 wherein said hub is positioned directly between and adjacent said spring and said diaphragm.

6. The instrument of claim 2 wherein said hub defines a hub passageway communicating said inner cutter with the source of vacuum.

7. The instrument of claim 6 wherein said diaphragm defines a diaphragm passageway communicating said hub passageway with the source of vacuum.

8. The instrument of claim 1 wherein said diaphragm assembly means includes an expanding and contracting bellows area at a generally rearward location thereof.

9. The instrument of claim 1 wherein said diaphragm assembly defines a debris passageway therethrough communicating the interior of said inner cutter with the source of vacuum.

10. The instrument of claim 1 wherein said diaphragm assembly includes a diaphragm against which air from the source of pressure directly impacts.

11. The instrument of claim 1 further comprising an adjustment means connected to said inner cutter for adjusting the normal position of said cutting surface relative to said port.

12. The instrument of claim 1 further comprising an infusion means connectable to a source of irrigation fluid for conducting irrigation fluid from the source of irrigation fluid to a site adjacent said port.

13. The instrument of claim 12 wherein said infusion means comprises an infusion cap which includes an infusion sleeve surrounding said outer cutter, and an infusion fitting communicating the source of irrigation fluid with said infusion sleeve.

14. The instrument of claim 13 further comprising a body member secured to said outer cutter and said infusion cap being fitted onto the distal end of said body member.

15. The instrument of claim 14 further comprising a sealing means disposed between said infusion cap and said body member for preventing the flow of irrigation fluid to the proximal end of said body member.

16. The instrument of claim 13 wherein said infusion sleeve defines at the distal end thereof at least one fluid opening around said outer cutter and out through which the irrigation fluid can flow.

17. The instrument of claim 16 wherein said at least one fluid opening comprises two fluid openings.

18. The instrument of claim 1 further comprising a gasket means at the proximal end of said outer cutter for preventing the flow of air between said inner and outer cutters.

19. The instrument of claim 1 further comprising a body member connected to said outer cutter and defining at least one relief opening through which air can pass between the interior and exterior of said body member as said diaphragm assembly is moved relative thereto and therein.

20. The instrument of claim 1 wherein said diaphragm assembly includes an annular diaphragm portion, and further comprising an end cap surrounding a portion of said diaphragm assembly, and an annular adapter sandwiched between said end cap and said annular diaphragm portion and defining a seal therebetween.

21. The instrument of claim 20 wherein said end cap defines an opening therethrough through which pressurized air from the source of pressure can flow and adjacent to said annular diaphragm portion so that the pressurized air directly impacts said annular diaphragm portion.

22. The instrument of claim 20 wherein said adapter is snap-fitted to the distal end of said end cap.

23. The instrument of claim 1 further comprising a body member to which said outer cutter is secured, and said biasing means comprising a spring operatively positioned between said diaphragm assembly and said body member.

24. The instrument of claim 23 wherein said diaphragm assembly includes at least one diaphragm surface, and said biasing means further comprises a communicating means for communicating the source of vacuum with said diaphragm surface to effect a sucking force on said diaphragm assembly.

25. The instrument of claim 1 further comprising an end cap to which a distal end of said diaphragm assembly is secured, and said end cap defining an end cap opening through which the source of vacuum can communicate with said port.

26. The instrument of claim 25 wherein said diaphragm assembly includes a distal portion thereof extending out through said end cap opening.

27. The instrument of claim 25 wherein said diaphragm assembly defines an expandable and contractable bellows portion positioned entirely within said end cap.

28. The instrument of claim 1 wherein said outer cutter defines a cutting surface at said port.

29. The instrument of claim 1 further comprising a body sleeve surrounding at least a portion of said outer cutter and whereby said instrument defines a posterior vitrectomy handpiece.

30. A surgical cutting instrument comprising:
a diaphragm assembly connectable to a source of pressure,
an inner cutter operatively connected to said diaphragm assembly, connectable to a source of vacuum, and defining a cutting surface,
an outer cutter positioned outside of said inner cutter and defining a suction port,
a biasing means for biasing said inner cutter against the bias caused by the force of the source of pressure on said inner cutter via said diaphragm assembly,
said biasing means and the operation of the source of pressure causing said cutting surface to reciprocate relative to said port and to thereby cut the matter drawn into said port by the operation of the source of vacuum, and
a body member secured to said outer cutter, an adjustment nut threadably received on said body member, an end cap, an adapter disposed between said adjustment nut and said end cap, and said adapter being operatively connected to said diaphragm assembly such that, when said adjustment nut is turned on said body member, said inner cutter is moved relative to said body member to thereby adjust the position of said cutting surface relative to said port.

31. The instrument of claim 1 including an interference fit between said adjustment nut and said body member providing a click noise when said adjustment nut is turned a predetermined amount on said body member.

32. The instrument of claim 1 wherein said predetermined amount is thirty degrees in either the clockwise or counterclockwise direction.

33. A surgical cutting instrument comprising:
a diaphragm assembly connectable to a source of pressure,
an inner cutter operatively connected to said diaphragm assembly, connectable to a source of vacuum, and defining a cutting surface,
an outer cutter positioned outside of said inner cutter and defining a suction port,
a biasing means for biasing said inner cutter against the bias caused by the force of the source of pressure on said inner cutter via said diaphragm assembly,
said biasing means and the operation of the source of pressure causing said cutting surface to reciprocate relative to said port and to thereby cut the matter drawn into said port by the operation of the source of vacuum, and
an end cap to which a distal end of said diaphragm assembly is secured, and said end cap defining an end cap opening through which the source of vacuum can communicate with said port,
said diaphragm assembly includes a distal portion thereof extending out through said end cap opening.

34. A surgical cutting instrument comprising:
a diaphragm assembly connectable to a source of pressure,
an inner cutter operatively connected to said diaphragm assembly, connectable to a source of vacuum, and defining a cutting surface,
an outer cutter positioned outside of said inner cutter and defining a suction port,
a biasing means for biasing said inner cutter against the bias caused by the force of the source of pressure on said inner cutter via said diaphragm assembly,
said biasing means and the operation of the source of pressure causing said cutting surface to reciprocate relative to said port and to thereby cut the matter drawn into said port by the operation of the source of vacuum, and
an end cap to which a distal end of said diaphragm assembly is secured, and said end cap defining an end cap opening through which the source of vacuum can communicate with said port,
said diaphragm assembly defines an expandable and contractible bellows portion positioned entirely within said end cap.

* * * * *